(12) United States Patent
Fujioka et al.

(10) Patent No.: US 7,338,479 B2
(45) Date of Patent: Mar. 4, 2008

(54) ABSORBENT ARTICLE WITH CUFF HAVING ADHESIVE OUTSIDE FIXED END INNER EDGE

(75) Inventors: Masaru Fujioka, Sadamitsu-cho (JP); Kenji Nakaoka, Sadamitsu-cho (JP); Kazuyo Mori, Sadamitsu-cho (JP); Taichiro Suzuki, Sadamitsu-cho (JP); Sayaka Sato, Aizumi-cho (JP)

(73) Assignee: Livedo Corporation, Ehime (JP)

( * ) Notice: Subject to any disclaimer, the term of this patent is extended or adjusted under 35 U.S.C. 154(b) by 176 days.

(21) Appl. No.: 10/515,593

(22) PCT Filed: Jun. 5, 2003

(86) PCT No.: PCT/JP03/07107

§ 371 (c)(1), (2), (4) Date: Nov. 24, 2004

(87) PCT Pub. No.: WO03/103555

PCT Pub. Date: Dec. 18, 2003

(65) Prior Publication Data

US 2005/0182380 A1    Aug. 18, 2005

(30) Foreign Application Priority Data

Jun. 5, 2002    (JP) .............................. 2002-164599

(51) Int. Cl.
*A61F 13/20* (2006.01)
(52) U.S. Cl. .......................... 604/385.24; 604/385.28; 604/385.101; 604/385.01
(58) Field of Classification Search ................. 604/385.24–385.28, 385.101, 385.01
See application file for complete search history.

(56) References Cited

U.S. PATENT DOCUMENTS

| | | | | |
|---|---|---|---|---|
| 4,795,454 A | * | 1/1989 | Dragoo .................. | 604/385.28 |
| 4,909,803 A | * | 3/1990 | Aziz et al. ............. | 604/385.28 |
| 5,021,051 A | * | 6/1991 | Hiuke .................... | 604/385.27 |
| 5,061,261 A | * | 10/1991 | Suzuki et al. .......... | 604/385.25 |
| 5,087,255 A | * | 2/1992 | Sims ..................... | 604/385.23 |
| 5,167,653 A | * | 12/1992 | Igaue et al. ............ | 604/385.04 |
| 5,403,301 A | * | 4/1995 | Huffman et al. ........ | 604/385.28 |
| 5,584,828 A | * | 12/1996 | Yamamoto et al. .... | 604/385.28 |
| 6,045,545 A | | 4/2000 | Vandemoortele et al. | |
| 6,142,985 A | | 11/2000 | Feist | |
| 6,248,098 B1 | | 6/2001 | Sayama | |
| 6,293,934 B1 | * | 9/2001 | Kumasaka ............. | 604/385.27 |
| 6,514,234 B2 | * | 2/2003 | Shimizu et al. ........ | 604/385.27 |
| 6,562,017 B1 | * | 5/2003 | Nakaoka et al. ....... | 604/385.28 |

FOREIGN PATENT DOCUMENTS

| | | |
|---|---|---|
| CN | 1214235 | 4/1999 |
| EP | 0 678 289 | 10/1995 |
| EP | 0 913 137 | 5/1999 |
| EP | 1 101 470 | 5/2001 |
| EP | 1 149 569 | 10/2001 |
| EP | 1 153 587 | 11/2001 |
| EP | 1 219 274 | 7/2002 |
| JP | 8-510940 | 11/1996 |
| JP | 2001-25485 | 1/2001 |
| JP | 2001-95839 | 4/2001 |
| WO | 94/18927 | 9/1994 |
| WO | 94/28840 | 12/1994 |

* cited by examiner

*Primary Examiner*—Michele Kidwell
(74) *Attorney, Agent, or Firm*—Wenderoth, Lind & Ponack, L.L.P.

(57) ABSTRACT

A bondable innermost edge e' of a hot melt adhesive to be applied to a base end 4a of each of a pair of raisable flaps 4 is disposed outside away from an inner edge 4d of the base end 4a in a state that each raisable flap 4 is folded into a multi-layered manner in bonding the base ends 4a of the raisable flaps 4 to an outer sheet at the opposite sides of an absorbent member 3 with the hot melt adhesive. This arrangement eliminates the likelihood that a free end 4b of each raisable flap 4 may be adhered to the base end 4a by an excessively and extensively applied adhesive portion even if the adhesive is excessively and extensively applied.

8 Claims, 7 Drawing Sheets

ABSORBENT ARTICLE WITH CUFF HAVING ADHESIVE OUTSIDE FIXED END INNER EDGE

TECHNICAL FIELD

The present invention relates to disposable absorbent articles capable of absorbing urine and other body exudates.

BACKGROUND ART

Figure 7:
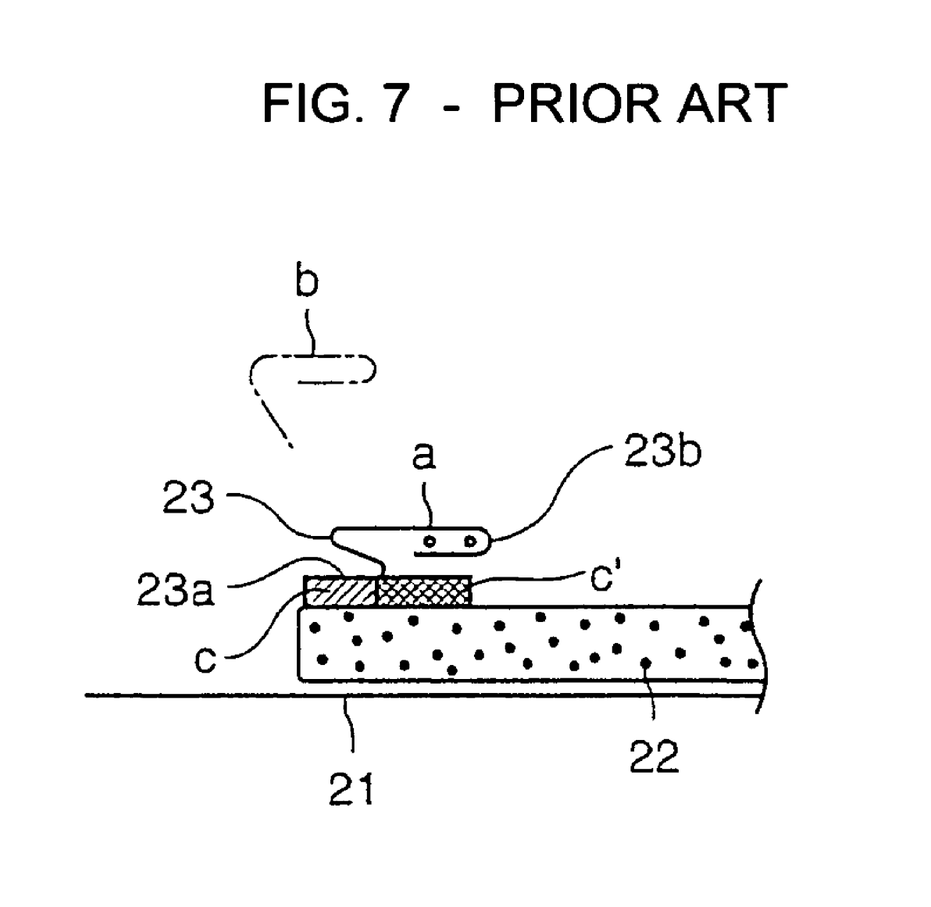
FIG. 7 is a schematic sectional view showing essential parts of a conventional disposable diaper.

Heretofore, there have been proposed absorbent articles, e.g. a disposable diaper shown in FIG. 7 schematically showing essential parts of the diaper in which an absorbent member 22 is attached to the skin-side surface of an outer sheet 21, and base ends 23a, 23a of raisable flaps 23, 23 are bonded to lateral sides on the top surface of the absorbent member 22, respectively (see WO94/28840; Japanese Unexamined Patent Publication (Tokuhyo) No. 8-510940).

The raisable flaps 23 disclosed in the above publication are adapted to prevent lateral leakage of urine and other body exudates by providing the free ends 23b which are rendered raisable from the folded line shown by the solid line a in FIG. 7 (see the two-dotted dashed line b in FIG. 7).

The above absorbent article is produced by applying a hot melt adhesive c at certain portions on the upper surface of the absorbent member 22 while feeding the absorbent member 22 at a high speed and by bonding the base ends 23a of the folded raisable flaps 23 to the adhesive portions of the absorbent member 22 to thereby bond the base ends 23a of the raisable flaps 23 to the upper surface of the absorbent member 22.

In the above production process, it is difficult to apply the hot melt adhesive c precisely at the predetermined portions. Specifically, let's presume a case that the hot melt adhesive c is applied to a portion (see the portion c' in FIG. 7) on the upper surface of the absorbent member 22 transversely inside relative to an inner edge of the base end 23a of the raisable flap 23. In such a case, if the inner edge of the free end 23b in a folded state of the raisable flap 23 is disposed inside relative to the inner edge of the base end 23a, it is highly likely that the free end 23b may be adhered to the upper surface of the absorbent member 22 by the adhesive portion c'. As a result, the adhered free end 23b cannot be rendered raisable, thereby failing to effectively prevent lateral leakage of urine and other body exudates.

The above mentioned drawback should be considered in connection with the following cases other than the above arrangement in which the base ends 23a of the raisable flaps 23 are bonded to the upper surface of the absorbent member 22. The other cases include an arrangement in which raisable flaps are bonded to the skin-side surface of an outer sheet at lateral sides of an absorbent member, and an arrangement in which an outer sheet includes a liquid impermeable back sheet and a top sheet having a smaller width than the back sheet with an absorbent member interposed between the back sheet and the top sheet, and base ends of waterproof or water repellent raisable flaps are bonded to the top sheet and the back sheet at lateral sides of the absorbent member.

In view of the above problems residing in the prior art, an object of the present invention is to provide an absorbent article capable of effectively preventing lateral leakage of urine and other body exudates by constantly and securely raisable free ends of raisable flaps.

DISCLOSURE OF THE INVENTION

An aspect of the present invention is directed to an absorbent article comprising: an outer sheet including a pair of leg fitting portions formed at opposite sides of a crotch portion between a front portion and a rear portion of the outer sheet; an absorbent member bonded to a crotch portion on a skin-side surface of the outer sheet; and a pair of raisable flaps each including a free end, the free end being bonded to an elastic member extending along front and rear directions of the outer sheet in an expanded state, wherein each of the raisable flaps includes a base end, and a bondable innermost edge of an adhesive to be applied to the base end is disposed outside away from an inner edge of the base end of the raisable flap in a state that the raisable flap is folded flat in bonding the base ends of the raisable flaps to the outer sheet at the opposite sides of the absorbent member by the adhesive.

In the above arrangement, the bondable innermost edge of the adhesive is disposed outside away from the inner edge of the base end in a state that each raisable flap is folded into a multi-layered manner in bonding the base ends of the raisable flaps to the outer sheet at the opposite sides of the absorbent member with an adhesive. This arrangement eliminates the likelihood that the free end of each raisable flap may be adhered to the base end by an excessively and extensively applied adhesive portion even if the adhesive is attempted to be excessively and extensively applied because the bondable innermost edge is disposed outside away from the inner edge of the base end.

DETAILED DESCRIPTION OF THE INVENTION

In the following, an embodiment of the present invention is described in detail referring to the accompanying drawings.

As shown in FIGS. 1 through 4, a disposable diaper 1, as an example of the inventive absorbent article, essentially comprises an outer sheet 2, an absorbent member 3, and a pair of raisable flaps 4 provided at lateral ends of the disposable diaper 1.

Figure 1:
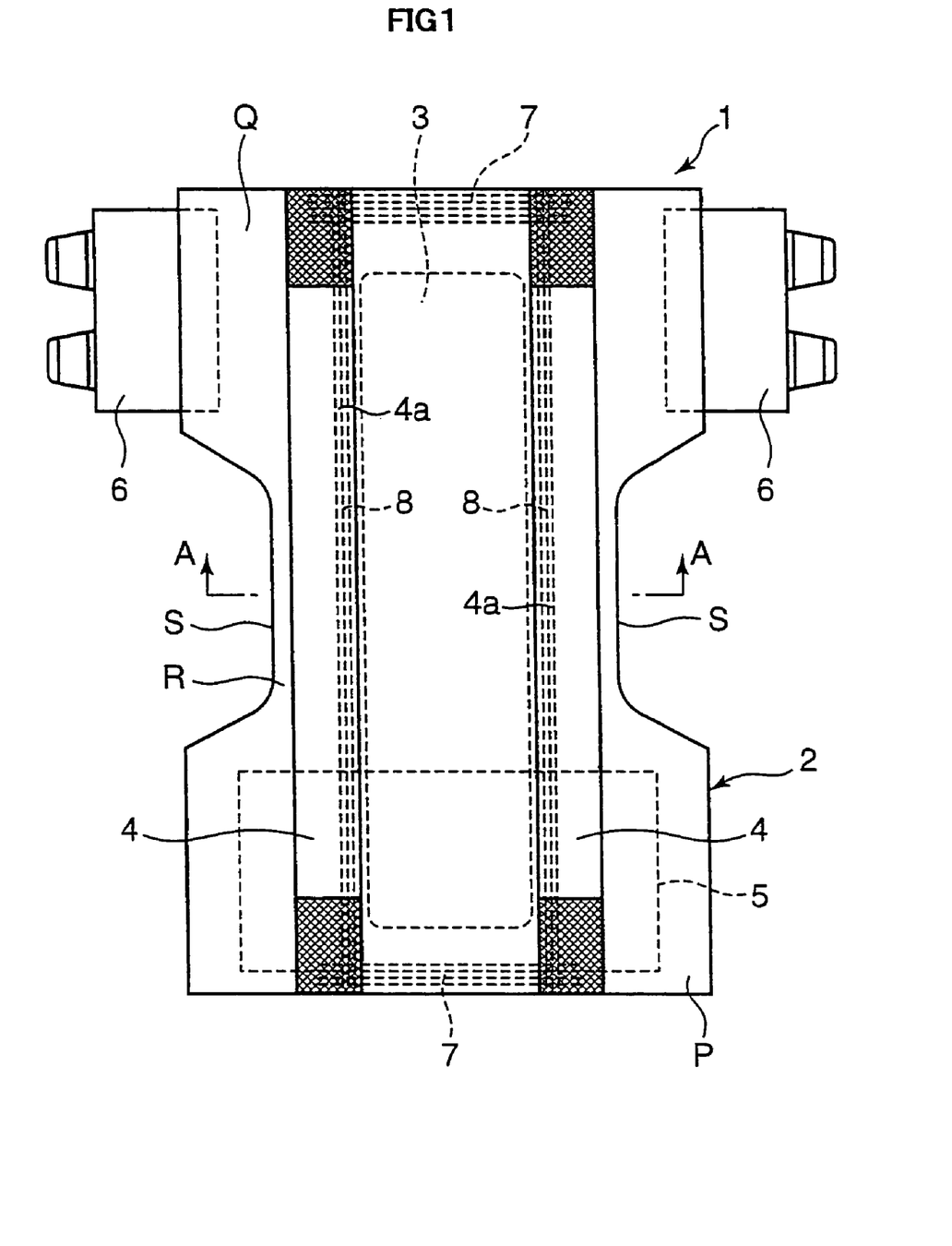
FIG. 1 is a front view of a disposable diaper in a developed state as an example of an absorbent article according to the present invention.
Figure 3:
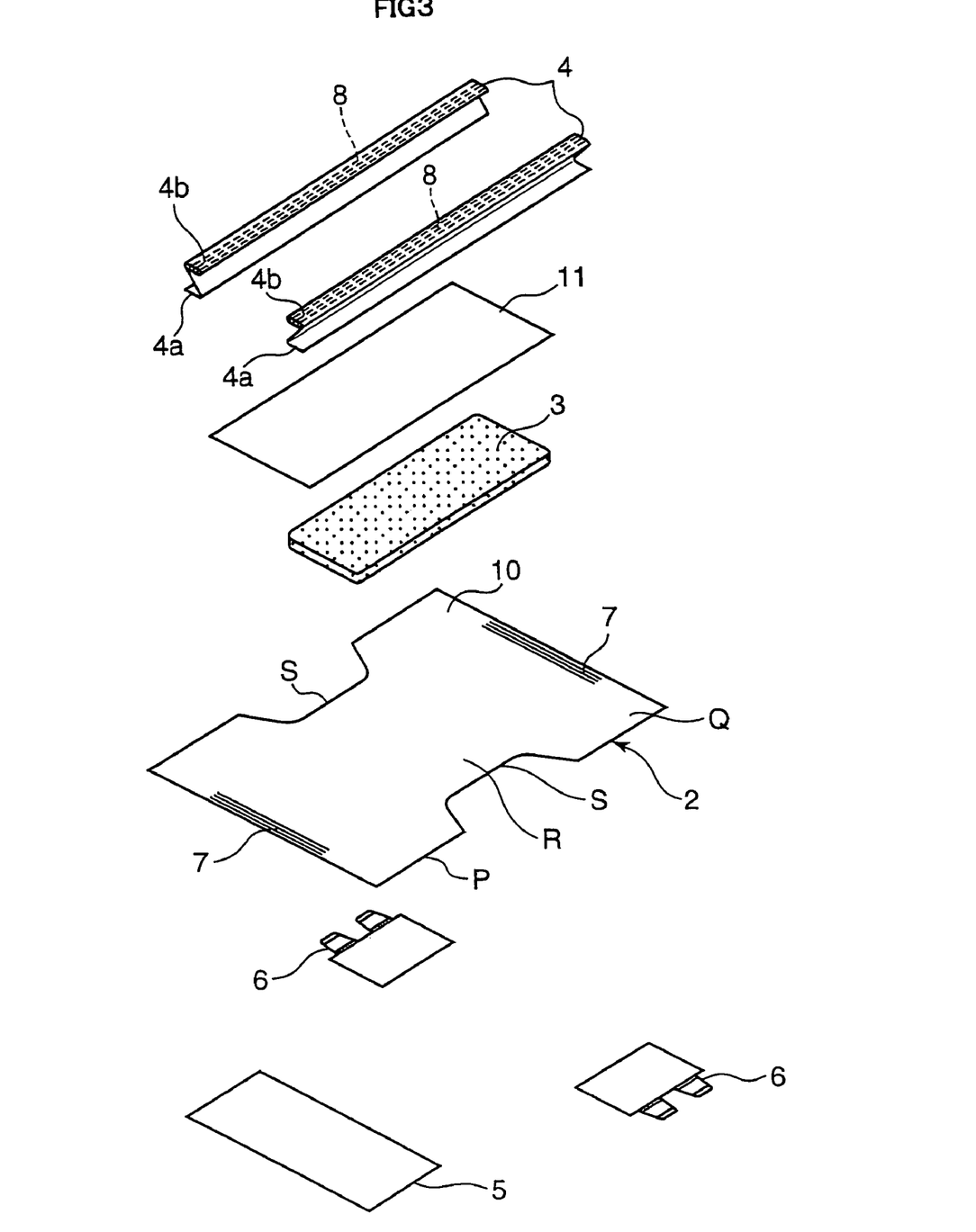
FIG. 3 is an exploded perspective view of the disposable diaper.

The outer sheet 2 has a liquid impervious back sheet 10 and a liquid pervious top sheet 11. The back sheet 10 has a shape substantially identical to the perimeter of the disposable diaper 1. Leg fitting portions S are formed at opposite sides of a crotch portion R between a front portion P and a rear portion Q of the back sheet 10. The top sheet 11 has a rectangular shape having a smaller width than the back sheet 10.

The back sheet 10 is in the form of a sheet including a thermoplastic resinous film such as a polyethylene film or a multi-layered sheet formed by laminating a non-woven fabric or woven fabric on the film. The film may have permeability capable of allowing permeation by water vapors. Alternatively, a leak-free multi-layered sheet formed by laminating a non-woven fabric having a high water repellency such as a melt-blown non-woven fabric of polypropylene on other liquid pervious non-woven fabric or woven fabric, or an impermeable non-woven fabric finished with water repellency may be used.

The top sheet 11 may be a liquid pervious non-woven or woven fabric made of synthetic fibers using polyester, polypropylene, polyethylene, or other thermoplastic resin as a raw material. Alternatively, natural fibers or a combination of natural fibers and synthetic fibers may be used.

Figure 2:
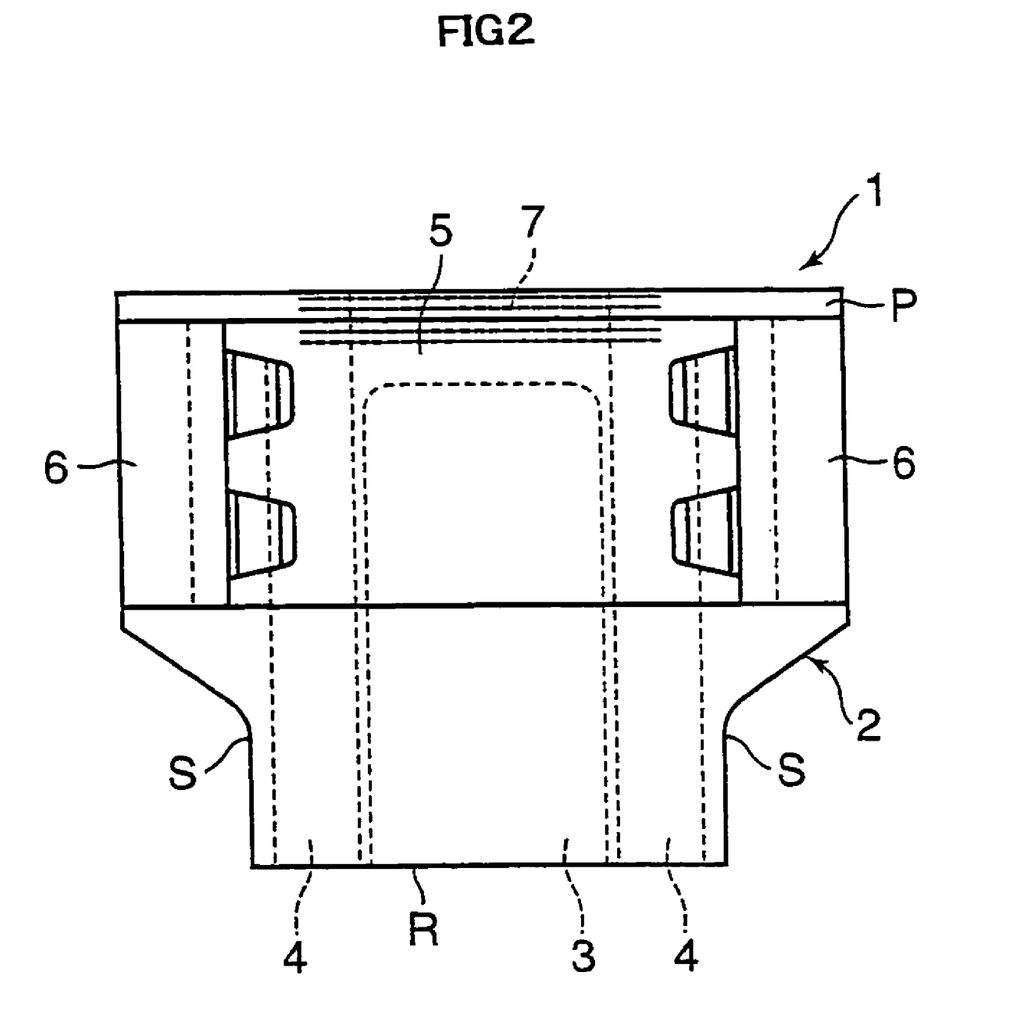
FIG. 2 is a front view of the disposable diaper in its used state.

A frontal tape 5 is attached to a bottom surface of the front portion P of the back sheet 10. Further, as shown in FIG. 2, fastening tapes 6 are attached to the opposite sides of the rear portion Q, respectively, so that the outer sheet 2 is configured into a three-dimensional shape by attaching the fastening tapes 6 to the frontal tape 5 in use of the disposable diaper 1. The frontal tape 5 and the fastening tapes 6 may be detachably attachable mechanical fasteners.

An elastic band member 7 for the waist of the wearer is attached to front and rear end portions of the back sheet 10 in an expanded state. The elastic member 7 extends between the back sheet 10 and the top sheet 11 in a state that the back sheet 10 is bonded to the top sheet 11 with a hot melt adhesive.

The absorbent member 3 extends along front and rear directions of the diaper substantially transversely in the middle of the back sheet 10. In bonding the top sheet 11 to the back sheet 10 by adhesive means d (see FIG. 4), the absorbent member 3 is disposed between the top sheet 11 and the back sheet 10.

The absorbent member 3 may be formed by mixing and laminating natural pulp fibers, synthetic fibers, and superabsorbent polymer powders. Preferably, the outer periphery of the absorbent member 3 may be covered with tissue paper.

The raisable flap 4 is configured in an accordion form as shown in FIGS. 4-6D and, in a preferred form, is folded into a substantially Z-shape in section. An elastic member 8 for the flap 4 is bonded to an inwardly oriented free end 4b formed at an upper portion of the raisable flap 4 in an expanded state. The elastic member 8 extends along the front and rear directions of the disposable diaper 1. The elastic member 8 may be made of polyurethane yarn, polyurethane film, natural rubber, polyurethane foam or the like. The elastic member 8 may be in the form of one or more bands.

The raisable flap 4 is a waterproof or water-repellent sheet-like member, and preferably may be a synthetic resinous non-woven fabric having water repellency in view of securing proper softness and comfortable skin contact.

The raisable flap 4 has an outwardly oriented base end (i.e., base end layer) 4a at a lower portion thereof. The base ends 4a of the raisable flaps 4 are disposed at lateral ends of the absorbent member 3, respectively. Each of the base ends 4a is bonded such that the base end 4a covers part of the back sheet 10 and a corresponding lateral end 11a of the top sheet 11 with a hot melt adhesive e. Further, front and rear parts of the free end (i.e., free end layer) 4b of each flap 4 shown by the cross-hatched portions in FIG. 1 are bonded to corresponding portions of the base end 4a.

Figure 4:
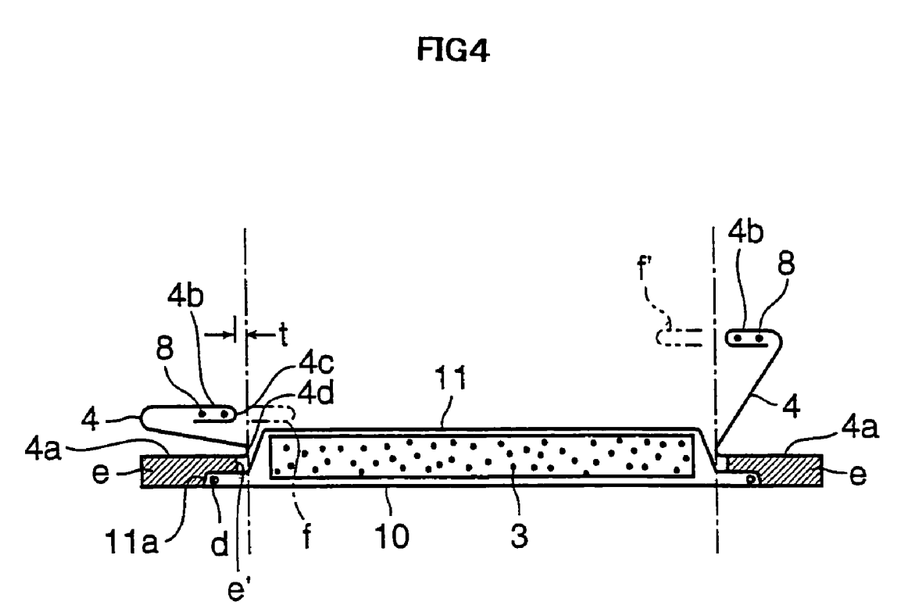
FIG. 4 is a schematic sectional view taken along the line A-A in FIG. 1.

In bonding the base end 4a of the raisable flap 4 to the corresponding lateral end 11a of the top sheet 11 and the back sheet 10 with the hot melt adhesive e, as shown on the left side in FIG. 4, an inner edge e' of the adhesive e to be applied to the base end 4a is located outside away from an inner edge 4d of the base end 4a by a distance t. The distance t (distance between the bondable innermost edge e' and the inner edge 4d of the base end 4a) is preferably in the range from 2 to 5 mm.

With the disposable diaper 1 having the above construction, as shown by the solid line on the right side in FIG. 4, the free end 4b of the raisable flap 4 is raised due to a contraction force of the elastic member 8 in a used state of the diaper 1 shown in FIG. 2.

In the above embodiment shown in FIG. 4, even if the hot melt adhesive e is attempted to be applied inside over a site corresponding to the bondable innermost edge e', there is no likelihood that the adhesive e extends over the inner edge 4d of the base end 4a because the sufficient distance t is provided. This arrangement prevents the likelihood that the free ends 4b may be adhered to the base ends owing to an excessively and inwardly extensively applied adhesive portion, and secures constant and stable raising of the free ends 4b of the raisable flaps 4, thereby effectively preventing lateral leakage of urine and other body exudates.

The embodiment shown in FIG. 4 is the one in which the flap 4 is folded and bonded in such a manner that the inner edge 4c of the free end 4b is located outside away from the inner edge 4d of the base end 4a. This embodiment is a most preferred embodiment because this embodiment eliminates the likelihood that the inner edge 4c of the free end 4b may be adhered to the base end 4a due to an excessively and inwardly extensively applied hot melt adhesive portion even if the hot melt adhesive is inadvertently applied inside to such an extent as to extend over the site corresponding to the bondable innermost edge e'. The present invention is made based on the idea that the bondable innermost edge e' is located outside away from the inner edge 4d of the base end 4a by the distance t. The present invention encompasses a modification (see the two-dotted dashed line f in FIG. 4) in which the flap is folded in such a manner that an inner edge 4c of a free end 4b is located inside relative to an inner edge 4d of a base end 4a.

Further, in the embodiment shown in FIG. 4, an inner edge 4c of a free end 4b may be located inside away from an inner edge 4d of a base end 4a, as shown by the two-dotted dashed line f on the right side in FIG. 4, as far as the free end 4b of the raisable flap 4 is raised in a used state.

In the above embodiment, the base ends 4a of the raisable flaps 4 are bonded in such a manner that the base ends 4a cover the lateral ends 11a of the top sheet 11 and parts of the back sheet 10. This arrangement is advantageous in preventing leakage of urine and other body exudates over the top sheet 11, through the top sheet 11, or out of the absorbent member 3 owing to the base ends 4a of the raisable flaps 4 bonded to the top sheet 11 and the back sheet 10.

Figure 5A:
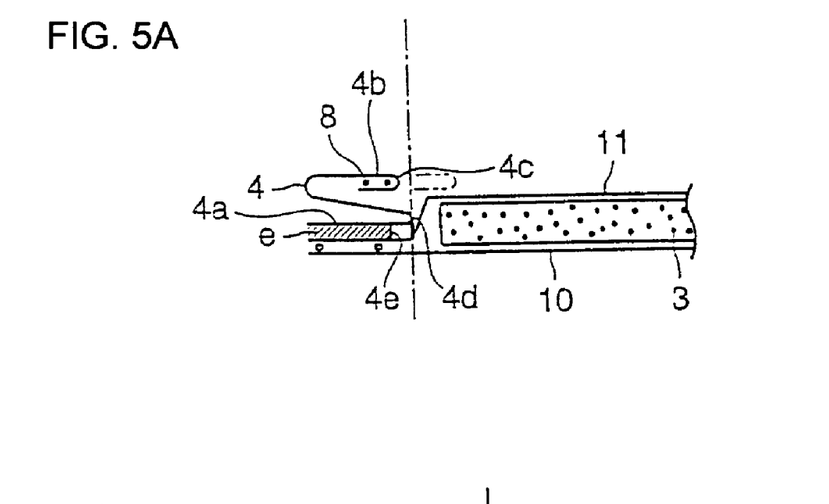
FIGS. 5A through 5C are schematic sectional views showing alterations of bonded sites of raisable flaps.

The above embodiment is directed to the arrangement in which the base ends 4a of the raisable flaps 4 are bonded to the lateral ends 11a of the top sheet 11 and the back sheet 10. As an altered form, as shown in FIG. 5A, a base end 4a of a raisable flap 4 may be bonded to a top sheet 11 as far as the top sheet 11 and a back sheet 10 have generally identical widths to each other. As further altered forms, a raisable flap 4 may be folded into a substantially U-shape as shown in FIGS. 5C, 6B, and 6D, which will be described in the following.

Figure 5B:
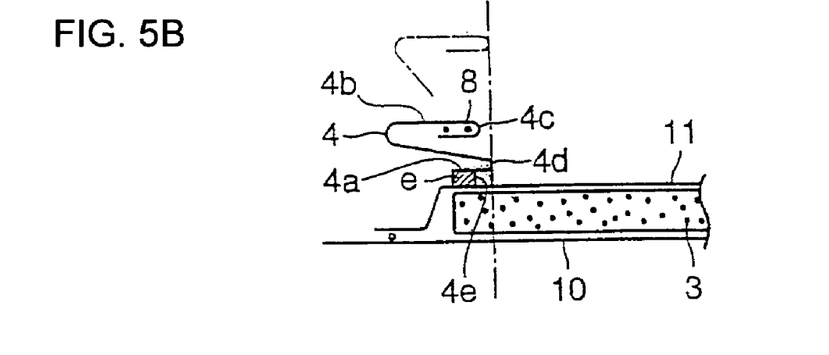
Figure 5C:
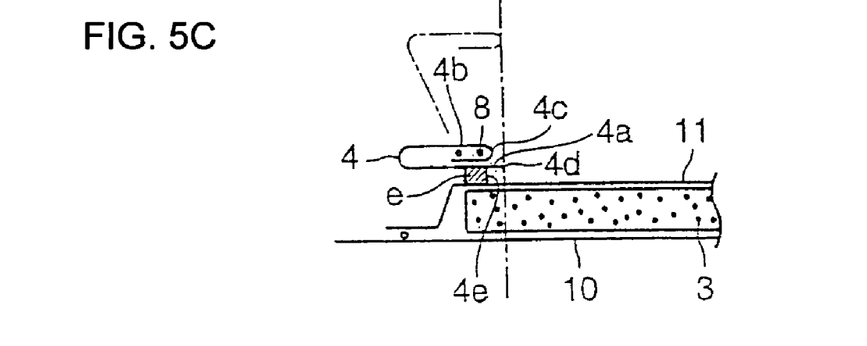

As yet another altered form, as shown in FIG. 5B, base ends 4a of raisable flaps 4 may be bonded to a top sheet 11 at lateral sides of an absorbent member 3. As still another altered form, a raisable flap 4 may be folded into a substantially U-shape, as shown in FIG. 5C.

Figure 6A:
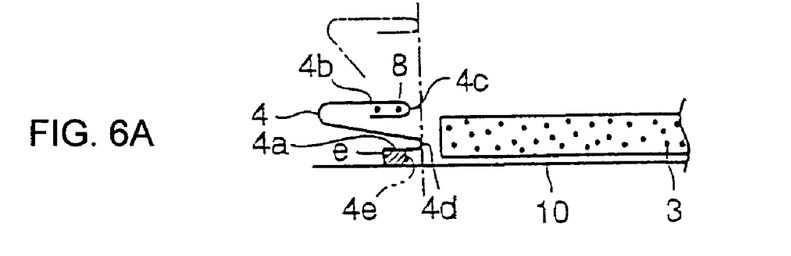
FIGS. 6A through 6D are schematic sectional views showing further alterations of the bonded sites of the raisable flaps.
Figure 6B:
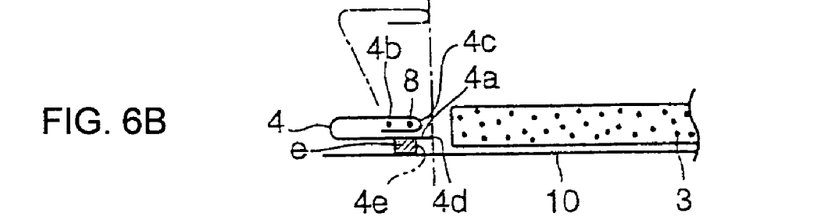

As a further altered form, as shown in FIG. 6A, in a diaper free of a top sheet 11, base ends 4a of raisable flaps 4 may be bonded to a back sheet 10 (corresponding to an outer sheet) on sides of an absorbent member 3. As a further altered form, a raisable flap 4 may be folded into a substantially U-shape, as shown in FIG. 6B.

Figure 6C:
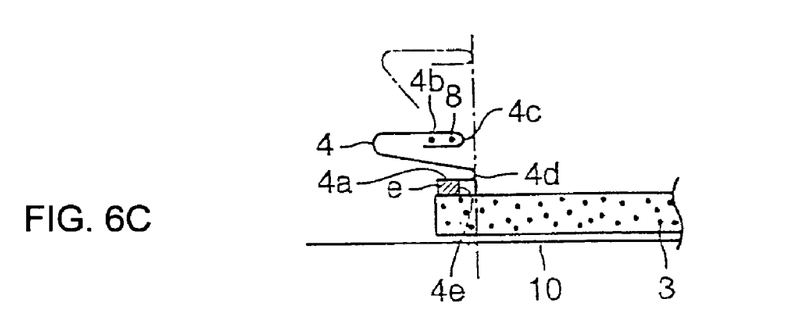
Figure 6D:
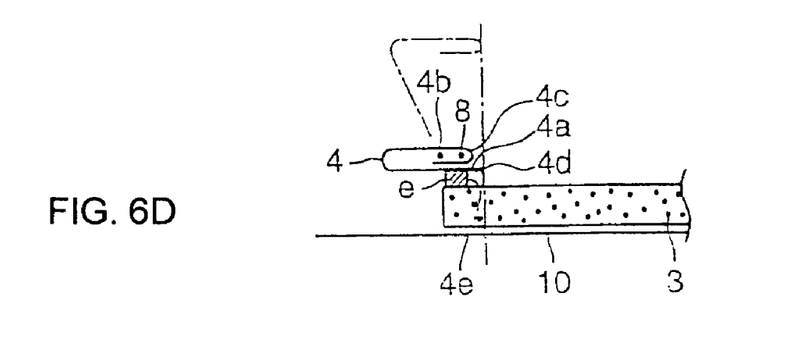

As yet another altered form, as shown in FIG. 6C, in a diaper free of a top sheet 11, base ends 4a of raisable flaps 4 may be bonded to lateral parts of an absorbent member 3. As another altered form, a raisable flap 4 may be folded into a substantially U-shape, as shown in FIG. 6D.

The present invention is described with respect to an open/close type disposable diaper attached with a tape, as a preferred embodiment. Alternatively, the present invention is applicable to incontinence pads and slip-on (pull-on) type disposable underwear. The disposable underwear can be produced with use of constituent elements optionally altered or modified by a person skilled in the art of the present invention.

INDUSTRIAL APPLICABILITY

As mentioned above, according to the present invention, the bondable innermost edge of an adhesive to be applied to the base end of each raisable flap is disposed outside away from the inner edge of the base end in a state that each raisable flap is folded into a multi-layered manner in bonding the base ends of the raisable flaps to the outer sheet at the opposite ends of the absorbent member by the adhesive portion. This arrangement eliminates likelihood that the free end of each of the raisable flaps may be adhered to the base end by an excessively and extensively applied adhesive portion even if the adhesive is inadvertently and inwardly extensively applied over the site corresponding to the bondable innermost edge because the bondable innermost edge is disposed outside away from the inner edge of the base end. This arrangement secures constant and stable raising of the free ends of the raisable flaps, thereby effectively preventing lateral leakage of urine and other body exudates.

The invention claimed is:

1. An absorbent article comprising:
    a back sheet including a front portion, a rear portion, a crotch portion, and a pair of leg fitting portions formed at opposite sides of said crotch portion between said front portion and said rear portion;
    an absorbent member bonded to said crotch portion of said back sheet on a skin-side surface of said back sheet;
    a pair of raisable flaps secured to said crotch portion of said back sheet at opposite sides of said absorbent member; and
    a pair of elastic members respectively bonded to said raisable flaps along front and rear directions of said back sheet in an expanded state;
    wherein each of said raisable flaps has multiple layers including a base end layer and a free end layer;
    wherein each of said raisable flaps has an adhesive portion provided on an underside of said base end layer to bond said base end layer relative to said absorbent member;
    wherein each of said elastic members is bonded to a respective one of said free end layers of said raisable flaps;
    wherein said base end layer of each of said raisable flaps has a base end layer inner edge, and a base end layer outer edge disposed outwardly of said base end layer inner edge;
    wherein said free end layer of each of said raisable flaps has a free end layer inner edge, and a free end layer outer edge disposed outwardly of said free end layer inner edge;
    wherein said multiple layers of each of said raisable flaps are configured in an accordion form so as to be movable between a folded condition in which said multiple layers are collapsed toward one another and in which said free end layer and said based end layer are both generally parallel with said back sheet, and a raised condition in which said multiple layers are separated relative to one another;
    wherein, for each of said raisable flaps when in said folded condition, said free end layer inner edge is disposed outside away from said base end layer inner edge; and
    wherein, for each of said raisable flaps when in said folded condition, an innermost edge of said adhesive portion is disposed outside away from said base end layer inner edge.

2. The absorbent article according to claim 1, wherein for each of said raisable flaps, said innermost edge of said adhesive portion is disposed outside away from said base end layer inner edge by a distance ranging from 2 to 5 mm.

3. The absorbent article according to claim 2, wherein for each of said raisable flaps, said accordion form having the multiple layers is in a Z-shaped form in section when in said folded condition.

4. The absorbent article according to claim 2, wherein for each of said raisable flaps, said accordion form having the multiple layers is in a U-shaped form in section when in said folded condition.

5. The absorbent article according to claim 1, wherein for each of said raisable flaps, said accordion form having the multiple layers is in a Z-shaped form in section when in said folded condition.

6. The absorbent article according to claim 1, wherein for each of said raisable flaps, said accordion form having the multiple layers is in a U-shaped form in section when in said folded condition.

7. The absorbent article according to claim 1, wherein each of said raisable flaps, when in said folded condition, has no portion extending directly from said base end layer inner edge inwardly beyond said base end layer inner edge.

8. The absorbent article according to claim 1, wherein each of said raisable flaps has no portion thereof bonded relative to said back sheet at a location inwardly of said innermost edge of said adhesive portion.

* * * * *